US012721553B2

(12) United States Patent
Tsai et al.

(10) Patent No.: US 12,721,553 B2
(45) Date of Patent: Sep. 1, 2026

(54) BLOOD OXYGEN CONCENTRATION MEASUREMENT DEVICE AND METHOD

(71) Applicant: Quanta Computer Inc., Taoyuan City (TW)

(72) Inventors: Peng-Zhe Tsai, Taoyuan City (TW); Yung-Ming Chung, Taoyuan City (TW)

(73) Assignee: QUANTA COMPUTER INC., Taoyuan City (TW)

( * ) Notice: Subject to any disclaimer, the term of this patent is extended or adjusted under 35 U.S.C. 154(b) by 393 days.

(21) Appl. No.: 18/507,388

(22) Filed: Nov. 13, 2023

(65) Prior Publication Data

US 2025/0040843 A1 Feb. 6, 2025

(30) Foreign Application Priority Data

Aug. 1, 2023 (TW) ................................ 112128839

(51) Int. Cl.
*A61B 5/1455* (2006.01)
*A61B 5/00* (2006.01)
*A61B 5/024* (2006.01)

(52) U.S. Cl.
CPC ...... *A61B 5/14551* (2013.01); *A61B 5/02416* (2013.01); *A61B 5/7246* (2013.01); *A61B 5/725* (2013.01)

(58) Field of Classification Search
CPC ............ A61B 5/14551; A61B 5/02416; A61B 5/7246; A61B 5/725; A61B 5/0205;

(Continued)

(56) References Cited

U.S. PATENT DOCUMENTS 5,431,170 A * 7/1995 Mathews ........... A61B 5/02433 600/323
5,853,364 A * 12/1998 Baker, Jr. ........... A61B 5/02416 600/323

(Continued)

FOREIGN PATENT DOCUMENTS

CN 110292372 A 10/2019
EP 2687154 A1 * 1/2014 ......... A61B 5/02416
TW 201821028 A 6/2018

OTHER PUBLICATIONS

Sakkarin et al. , A Photoplethysmographic Signal Isolated From an Additive Motion Artifact by Frequency Translation, Aug. 2018, IEEE Transactions on Biomedical Circuits and Systems, vol. 12, No. 4. pp. 904-917 (Year: 2018).*

(Continued)

*Primary Examiner* — Brian L Casler
(74) *Attorney, Agent, or Firm* — McClure, Qualey & Rodack, LLP

(57) ABSTRACT

A blood oxygen concentration measurement device includes a light source unit, a light detection unit, a sensing unit and a control unit. The light source generates a light signal. The light detection unit receives a penetrating signal generated by the light signal penetrating an object to generate a detection signal. The sensing unit senses movement of the blood oxygen concentration measurement device to output a sensing signal. The processing unit receives the detection signal and the sensing signal, and calculates a blood oxygen value and a pulse rate according to the detection signal and the sensing signal.

11 Claims, 11 Drawing Sheets

(58) Field of Classification Search
CPC .............. A61B 5/14552; A61B 5/7203; A61B 5/02438; A61B 5/02444; A61B 5/0261; A61B 5/024; A61B 5/7235; A61B 5/7239; A61B 5/7242; A61B 5/7257; A61B 5/7253; A61B 5/1118; A61B 5/1123; A61B 5/1455; A61B 5/7221; A61B 5/7207; A61B 5/721; A61B 5/7214; A61B 5/7225; A61B 5/11; A61B 5/14542
USPC .......................................................... 600/323
See application file for complete search history.

(56) References Cited

U.S. PATENT DOCUMENTS 6,002,952 A * 12/1999 Diab .................... A61B 5/7278 600/502
6,035,223 A * 3/2000 Baker, Jr. ............. A61B 5/0059 600/323
6,094,592 A * 7/2000 Yorkey .............. A61B 5/14551 600/475
2005/0033129 A1* 2/2005 Edgar .................. A61B 5/7207 600/323
2017/0181680 A1* 6/2017 Baek ...................... A61B 5/725
2018/0160955 A1 6/2018 Lin et al.

OTHER PUBLICATIONS

Chinese language office action dated Jan. 4, 2024, issued in application No. TW 112128839.

* cited by examiner

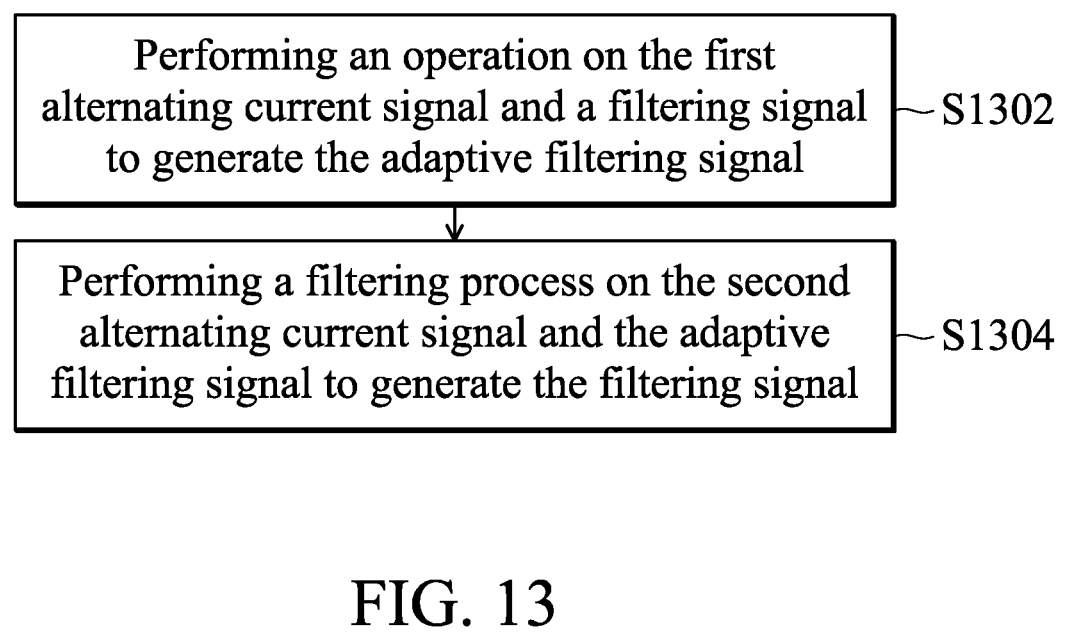

Performing an operation on the first alternating current signal and a filtering signal to generate the adaptive filtering signal — S1302

Performing a filtering process on the second alternating current signal and the adaptive filtering signal to generate the filtering signal — S1304

FIG. 13

BLOOD OXYGEN CONCENTRATION MEASUREMENT DEVICE AND METHOD

CROSS REFERENCE TO RELATED APPLICATIONS

This application claims priority of Taiwan Patent Application No. 112128839, filed on Aug. 1, 2023, the entirety of which is incorporated by reference herein.

BACKGROUND OF THE INVENTION

Field of the Invention

The present invention relates to a measurement device and method, and in particular it relates to a blood oxygen concentration measurement device and method.

Description of the Related Art

In general, the current method of measuring blood oxygen concentration requires that the patient be in a static state in order to measure blood oxygen concentration (pulse oximetry, SpO2) and pulse rate (PR), with a reference value. Physical activity may generate a motion artifact, making the measurement of blood oxygen concentration and pulse rate inaccurate, often resulting in false values and a false alarm of low blood oxygen. In addition, since patients often need to continuously monitor the blood oxygen concentration over a long period of time, it is inevitable that there may be finger movement and physical activity, which causes shaking noise and causes inaccuracies in the measurement of blood oxygen concentration and pulse rate. Therefore, how to effectively increase the accuracy of measuring blood oxygen concentration and pulse rate has become a focus for technical improvements by various manufacturers.

BRIEF SUMMARY OF THE INVENTION

An embodiment of the present invention provides a blood oxygen concentration measurement device and method, thereby increasing the accuracy of the blood oxygen concentration measurements under the object actives, and increasing the convenience of use.

An embodiment of the present invention provides a blood oxygen concentration measurement device, which includes a light source unit, a light detection unit, a sensing unit and a processing unit. The light source unit is configured to generate a light signal. The light detection unit is configured to receive a penetrating signal generated by the light signal penetrating an object to generate a detection signal. The sensing unit is configured to sense movement of the blood oxygen concentration measurement device to output a sensing signal. The processing unit is configured to receive the detection signal and the sensing signal, and calculate a blood oxygen value and a pulse rate according to the detection signal and the sensing signal.

An embodiment of the present invention provides a blood oxygen concentration measurement method, which includes the following steps. A light source unit is used to generate a light signal. A light detection unit is used to receive a penetrating signal generated by the light signal penetrating an object to generate a detection signal. A sensing unit is used to sense movement of the blood oxygen concentration measurement device to output a sensing signal. A processing unit is used to receive the detection signal and the sensing signal, and calculate a blood oxygen value and a pulse rate according to the detection signal and the sensing signal.

According to the blood oxygen concentration measurement device and method disclosed by the present invention, the light detection unit receives the penetrating signal generated by the light signal penetrating the object to generate the detection signal, the sensing unit senses the movement of the blood oxygen concentration measurement device to output the sensing signal, and the processing unit calculates the blood oxygen value and the pulse rate according to the detection signal and the sensing signal. Therefore, the accuracy of the blood oxygen concentration measurement may be effectively increased under the object actives, and the convenience of use is increased.

BRIEF DESCRIPTION OF THE DRAWINGS

The present invention can be more fully understood by reading the subsequent detailed description and examples with references made to the accompanying drawings, wherein:

FIG. 13 is a detailed flowchart of step S1206 in FIG. 12; and

DETAILED DESCRIPTION OF THE INVENTION

In each of the following embodiments, the same reference number represents an element or component that is the same or similar.

Figure 1:
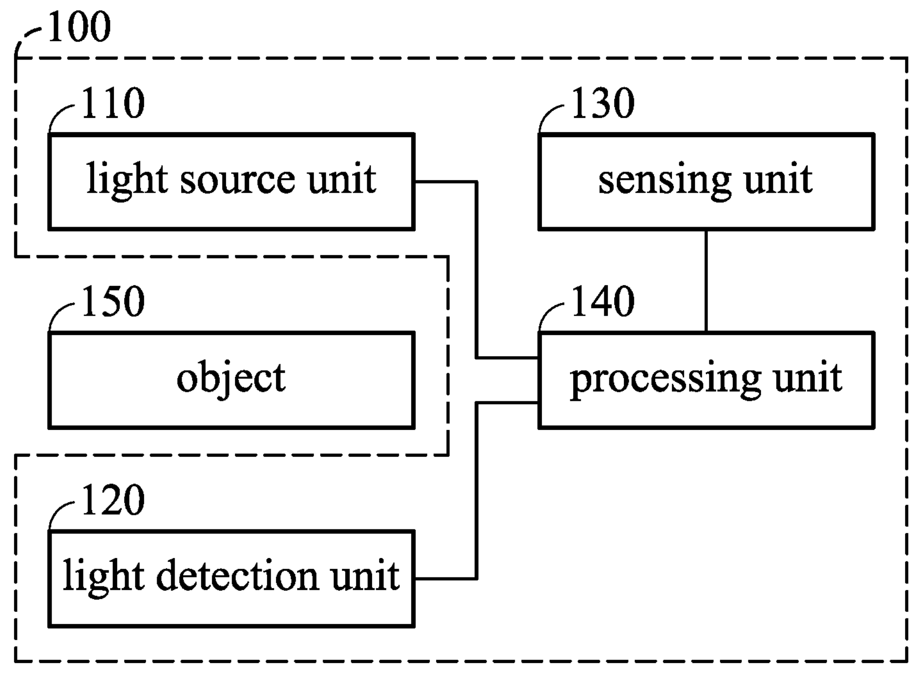
FIG. 1 is a schematic view of a blood oxygen concentration measurement device according an embodiment of the present invention.

FIG. 1 is a schematic view of a blood oxygen concentration measurement device according an embodiment of the present invention. Please refer to FIG. 1. The blood oxygen concentration measurement device 100 includes a light source unit 110, a light detection unit 120, a sensing unit 130 and a processing unit 140.

The light source unit 110 may generate a light signal. In the embodiment, the light source unit 110 may include a red light-emitting diode and an infrared light-emitting diode, and the light signal may include a red light signal and an infrared light signal, but the embodiment of the present invention is not limited thereto.

The light detection unit 120 may receive a penetrating signal generated by the light signal penetrating an object 150 to generate a detection signal. That is, the light detection unit 120 may be disposed opposite to the light source unit 110, and the object 150 may be placed between the light source unit 110 and the light detection unit 120. Accordingly, the light source unit 110 may generate the light signal to the object 150, the light signal may penetrate the object 150 to generate the penetrating signal, the penetrating signal may be transmitted to the light detection unit 120, and the light detection unit 120 receives the penetrating signal to generate the corresponding detection signal.

In the embodiment, the above object 150 is, for example, a finger of a user, but the embodiment of the present invention is not limited thereto. In addition, the light detection unit 120 may be a photodiode or another suitable photodetector, and the detection signal may be a current signal of a photoplethysmogram (PPG) signal, but the embodiment of the present invention is not limited thereto. Furthermore, the detection signal may include a first alternating current signal and a first direct current signal, wherein the first alternating current signal may include a red light alternating current signal and an infrared light alternating current signal, and the first direct current signal may include a red light direct current signal and an infrared light direct current signal.

The sensing unit 130 may sense movement of the blood oxygen concentration measurement device 100 to output a sensing signal. In the embodiment, the sensing unit 130 is, for example, a G-sensor, but the embodiment of the present invention is not limited thereto. In addition, the sensing signal may include a second alternating current signal and a second direct current signal, wherein the second alternating current signal may include a three-axis alternating current signal, the second direct current signal may include a three-axis direct current signal, and the above three-axis may be X axis, Y axis and Z axis.

The processing unit 140 may be coupled to the light source unit 110, the light detection unit 120 and the sensing unit 130. The processing unit 140 may provide a driving signal to the light source unit 110, so that the light source unit 110 may generate the light signal to the object 150. In addition, the processing unit 140 may receive the detection signal and the sensing signal. Afterward, the processing unit 140 may calculate a blood oxygen value (blood oxygen saturation, SpO2) and a pulse rate (PR) according to the detection signal and the sensing signal. In the embodiment, the processing unit 140 may be a micro control unit (MCU) or another suitable controller, but the embodiment of the present invention is not limited thereto.

Furthermore, the processing unit 140 may obtain a first alternating current signal and a first direct current signal from the detection signal and obtain a second alternating current signal from the detection signal. In the embodiment, the processing unit 140 performs a filtering on the detection signal through a band pass filter, for example, so as to obtain the first alternating current signal of the detection signal. The processing unit 140 performs the filtering on the detection signal through a low pass filter, for example, so as to obtain the first direct current signal of the detection signal. The processing unit 140 performs the filtering on the detection signal through the detection signal through the band pass filter, for example, so as to obtain the second alternating current signal of the detection signal.

Figure 2:
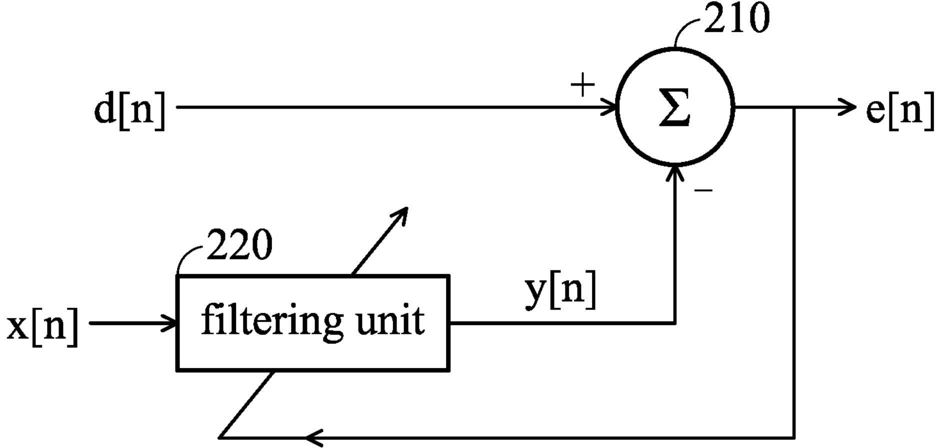
FIG. 2 is a schematic view of a structure of an adaptive filtering process of a processing unit according an embodiment of the present invention.

Then, the processing unit 140 performs an adaptive filtering process on the first alternating current signal and the second alternating current signal to generate an adaptive filtering signal. In some embodiments, the processing unit 140 may include an operation unit 210 and a filtering unit 220, as shown in FIG. 2. The operation unit 140 may receive the first alternating current signal and a filtering signal, and perform an operation on the first alternating current signal d[n] and the filtering signal y[n] to generate the adaptive filtering signal. In the embodiment, the operation unit 140 may be a subtractor, performing a subtraction operation on the first alternating current signal d[n] and the filtering signal y[n] to generate the adaptive filtering signal e[n]. The filtering unit 220 may be coupled to the operation unit 210. The filtering unit 220 may receive the second alternating current signal x[n] and the adaptive filtering signal e[n], perform the filtering process on the second alternating current signal x[n] and the adaptive filtering signal e[n] to generate the filtering signal y[n] and output the filtering signal to the operation unit 210. Therefore, it may effectively remove noise the noise generated by the activity (moving or shaking) of the object 150.

In addition, the above adaptive filtering process of the processing unit 140 may be shown in equation (1), equation (2) and equation (3).

$$y[n]=\sum_{i=0}^{M-1} w_i[n]*x[n] \tag{1}$$

$$e[n]=d[n]-y[n] \tag{2}$$

$$w_i[n+1]=w_i[n]+Mu*x[n-1]*e[n] \tag{3}$$

wherein d[n] is the first alternating current signal, x[n] is the second alternating current signal, e[n] is the adaptive filtering signal, y[n] is the filtering signal, $w_i[n]$ is a filter coefficient, M is a constant, and Mu*x[n−1]*e[n] is a correction factor of the filter coefficient.

Afterward, the processing unit 140 converts the adaptive filtering signal and the second alternating current signal to generate a first spectrum and a second spectrum. Furthermore, the processing unit 140 may perform a fast Fourier transform (FFT) on the adaptive filtering signal and the second alternating current signal to generate the first spectrum and the second spectrum. In some embodiments, the first spectrum may be as shown in FIG. 3, FIG. 4, FIG. 5, FIG. 7 or FIG. 9, and the second spectrum may be as shown in FIG. 6, FIG. 8 or FIG. 10.

In FIG. 3, FIG. 4, FIG. 5, FIG. 7 or FIG. 9, the reference number "FR1" represents a first frequency range, the reference number "FR2" represents a second frequency range, the reference number "FR3" represents a third frequency range, the reference number "FR5" represents a fifth frequency range, the reference number "FR6" represents a sixth frequency range, the reference numbers "301", "401", "501", "701" and "901" represent a first maximum peak value, the reference numbers "302", "402", "502", "702" and "902" represent a second maximum peak value, the reference numbers "303" and "403" represent a third maximum peak value, the reference numbers "703" and "903" represent a fifth maximum peak value, the reference numbers "704" and "904" represent a sixth maximum peak value, the reference number "S1" represents the first alternating current signal, the reference number "S11" represents the infrared light alternating current signal, and the reference number "S12" represents the red light alternating current signal.

In the embodiment, the first alternating current signal S1 may include the infrared light alternating current signal S11 and the red light alternating current signal S12. For the convenience of explanation, in FIG. 3, FIG. 4, FIG. 5, FIG. 7 or FIG. 9, only the maximum peak value of the infrared light alternating current signal S11 is represented, i.e., the first maximum peak values 301, 401, 501, 701 and 901, the second maximum peak values 302, 402, 502, 702 and 902, the third maximum peak values 303 and 403, the fifth maximum peak values 703 and 903, and the sixth maximum peak values 704 and 904 are the maximum peak values of the infrared light alternating current signal S11. In addition, the frequency corresponding to the red light alternating current signal S12 may be the same as the frequency corresponding to the infrared light alternating current signal S11.

Figure 3:
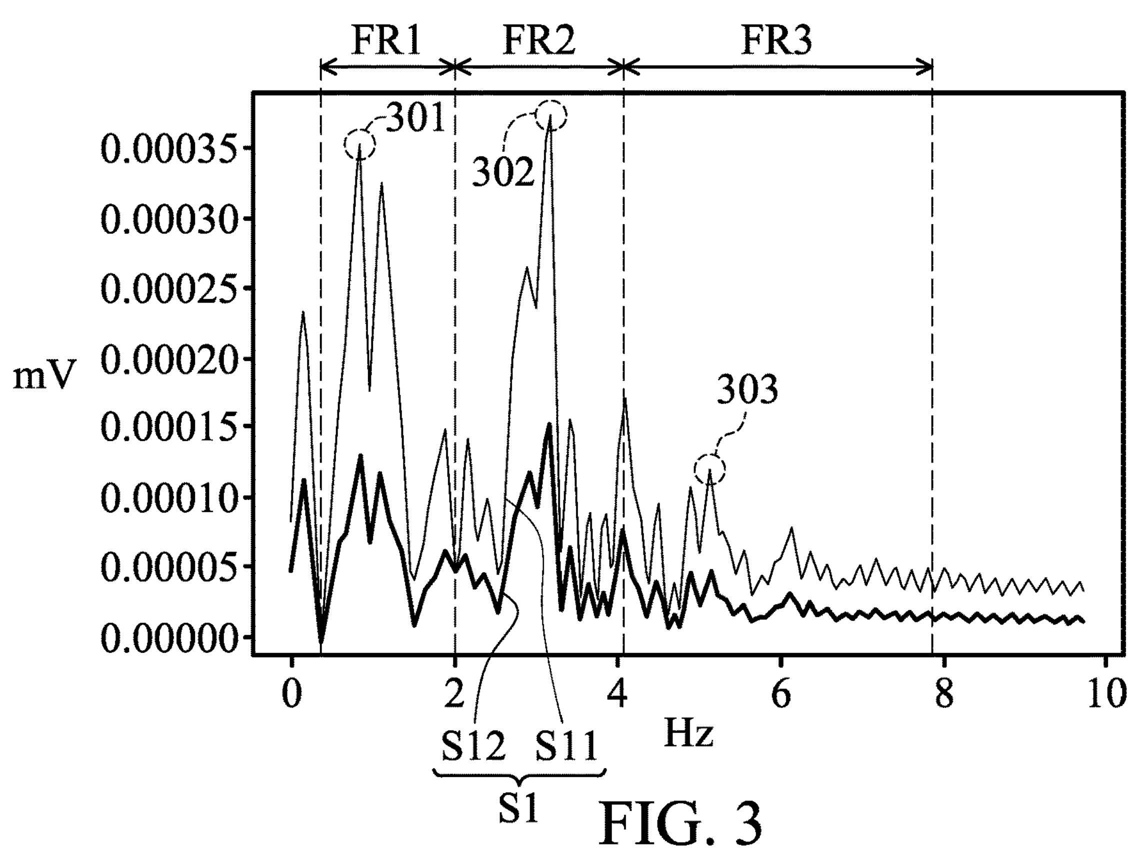
FIG. 3 is a waveform diagram of a first spectrum according an embodiment of the present invention.

Therefore, after obtaining the maximum peak value of the infrared light alternating current signal S11, the maximum peak value of the red light alternating current signal S12 may be obtained through the frequency corresponding to the maximum peak value of the infrared light alternating current signal S11. For example, FIG. 3 is taken as an example, when the maximum peak value (such 301) of the infrared light alternating current signal S11 is about 0.00035 mV and the frequency corresponding to the maximum peak value (such 301) of the infrared light alternating current signal S11 is 0.8 Hz, the maximum peak value of the red light alternating current signal S12 is about 0.00013 mV. The rest of corresponding relationship between the maximum peak value of the infrared light alternating current signal S11 and the maximum peak value of the red light alternating current signal S12 may be deduced by analogy.

In FIG. 6, FIG. 8 or FIG. 10, the reference number "FR4" represents the fourth frequency range, the reference numbers "601", "801" and "1001" represent a fourth maximum peak value, and the reference number "S2" represents the second alternating current signal.

Then, the processing unit 140 may search a maximum peak value corresponding to the first alternating current signal according to the first spectrum and the second spectrum, and calculate the blood oxygen value and the pulse rate according to the maximum peak value and the first direct current signal. In addition, the above maximum peak value includes the maximum peak value of the red light alternating current signal (such as S12) and the maximum peak value of the infrared light alternating current signal (such as S11).

In the embodiment, the blood oxygen value may be calculated according to the maximum peak value of the red light alternating current signal (such as S12), the maximum peak value of the infrared light alternating current signal (such as S11), the direct current level of the red light direct current signal and the direct current level of the infrared light direct current signal. For example, the blood oxygen value=(the maximum peak value of the red light alternating current signal (such as S12)/the direct current level of the red light direct current signal)/(the maximum peak value of the infrared light alternating current signal (such as S11)/the direct current level of the infrared light direct current signal). The pulse rate may be calculated according to the frequency corresponding to the red light alternating current signal (such as S12) or the infrared light alternating current signal (such as S11).

In some embodiments, the processing unit 140 may use a first frequency range (such as FR1) to search a first maximum peak value (such as 301, 401, 501, 701 or 901) in the first spectrum. The processing unit 140 may use a second frequency range (such as FR2) to search a second maximum peak value (such as 302, 402, 502, 702 or 902) in the first spectrum. The processing unit 140 may use a third frequency range (such as FR3) to search a third maximum peak value (such as 303 or 403). The processing unit 140 may use a fourth frequency range (such as FR4) to search a fourth maximum peak value (such as 601, 602 or 1001) in the second spectrum.

In some embodiments, the first frequency range (such as FR1) may partially overlap the second frequency range (such as FR2), the second frequency range (such as FR2) may not overlap the third frequency range (such as FR3), and the second frequency range (such as FR2) may overlap the fourth frequency range (such as FR4). For example, the first frequency range (such as FR1) is, for example, 0.4 Hz~2 Hz, the second frequency range (such as FR2) is, for example, 0.4 Hz~4 Hz, the third frequency range (such as FR3) is, for example, 4 Hz~8 Hz, and the fourth frequency range (such as FR4) is, for example, 0.4~4 Hz, but the embodiment of the present invention is not limited thereto.

Figure 4:
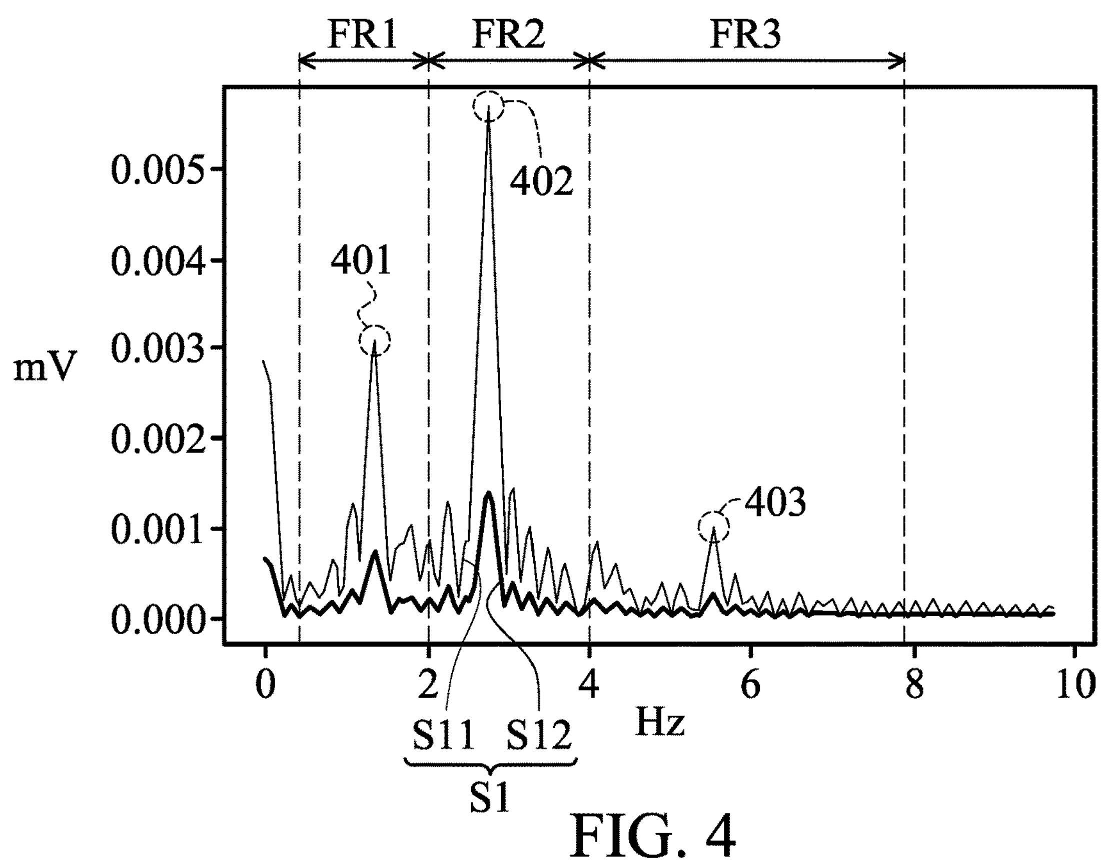
FIG. 4 is a waveform diagram of a first spectrum according an embodiment of the present invention.

Then, the processing unit 140 may determine that the first maximum peak value is the same as the second maximum peak value. As shown in FIG. 3 or FIG. 4, when determining that the first maximum peak value (such as 301 or 401) is not the same as the second maximum peak value (such as 302 or 402), the processing unit 140 may determine whether the frequency corresponding to the second maximum peak value (such as 302 or 402) is related to the frequency corresponding to the third maximum peak value (such as 303 or 403).

In the embodiment, whether the frequency corresponding to the second maximum peak value is related to the frequency corresponding to the third maximum peak value indicates whether the frequency corresponding to the third maximum peak value is a multiple of the frequency corresponding to the second maximum peak value. For example, when the frequency corresponding to the second maximum peak value is about 3 Hz and the frequency corresponding to the third maximum peak value is about 6 Hz, it indicates that the frequency corresponding to the second maximum peak value is related to the frequency corresponding to the third maximum peak value, and the frequency corresponding to the third maximum peak value is the multiple of the frequency corresponding to the second maximum peak value. When the frequency corresponding to the second maximum peak value is about 3 Hz and the frequency corresponding to the third maximum peak value is about 5 Hz, it indicates that the frequency corresponding to the second maximum peak value is not related to the frequency corresponding to the third maximum peak value, and the frequency corresponding to the third maximum peak value is not the multiple of the frequency corresponding to the second maximum peak value. The rest of corresponding relationship between the frequency corresponding to the second maximum peak value and the frequency corresponding to the third maximum peak value may be deduced by analogy.

As shown in FIG. 3, when the frequency corresponding to the second maximum peak value (such as 302) is not related to the frequency corresponding to the third maximum peak value (such as 303), the processing unit 140 may use the first maximum peak value (such as 301) as the maximum peak value corresponding to the first alternating current signal, calculate the blood oxygen value according to the first maximum peak value (such as 301) and the first direct current signal, and calculate the pulse rate according to the frequency corresponding to the first maximum peak value (such as 301).

As shown in FIG. 4, when the frequency corresponding to the second maximum peak value (such as 402) is related to the frequency corresponding to the third maximum peak value (such as 403), the processing unit 140 may use the second maximum peak value (such as 402) as the maximum peak value corresponding to the first alternating current signal, calculate the blood oxygen value according to the second maximum peak value (such as 402) and the first direct current signal, and calculate the pulse rate according to the frequency corresponding to the second maximum peak value (such as 402).

Continued to the processing unit 140 determining whether the first maximum peak value is the same as the second maximum peak value, as shown in FIG. 5 and FIG. 6, FIG. 7 and FIG. 8, or FIG. 9 and FIG. 10, when determining that the first maximum peak value (such as 501, 701 or 901) is the same as the second maximum peak value (such as 502, 702 or 902), the processing unit 140 may determine whether the frequency corresponding to the first maximum peak value (such as 501, 701 or 901) is the same as the frequency corresponding to the fourth maximum peak value (such as 601, 801 or 1001).

Figure 5:
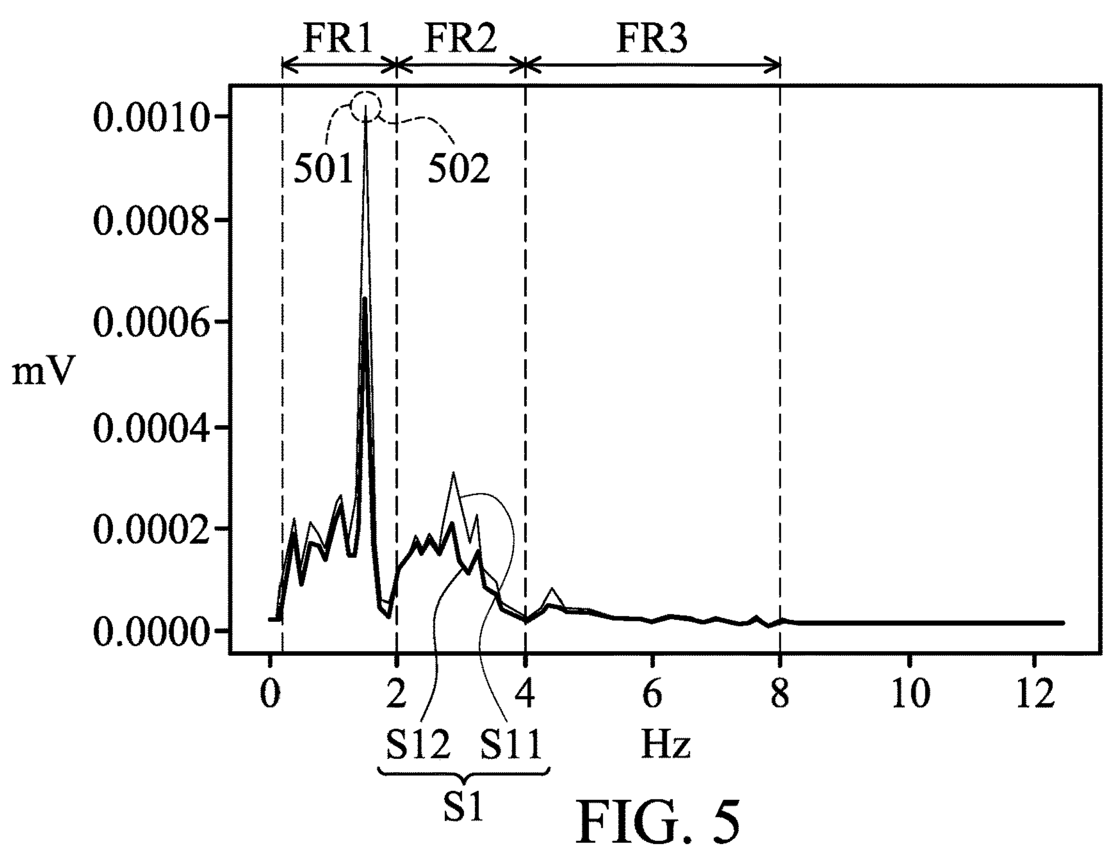
FIG. 5 is a waveform diagram of a first spectrum according an embodiment of the present invention.
Figure 6:
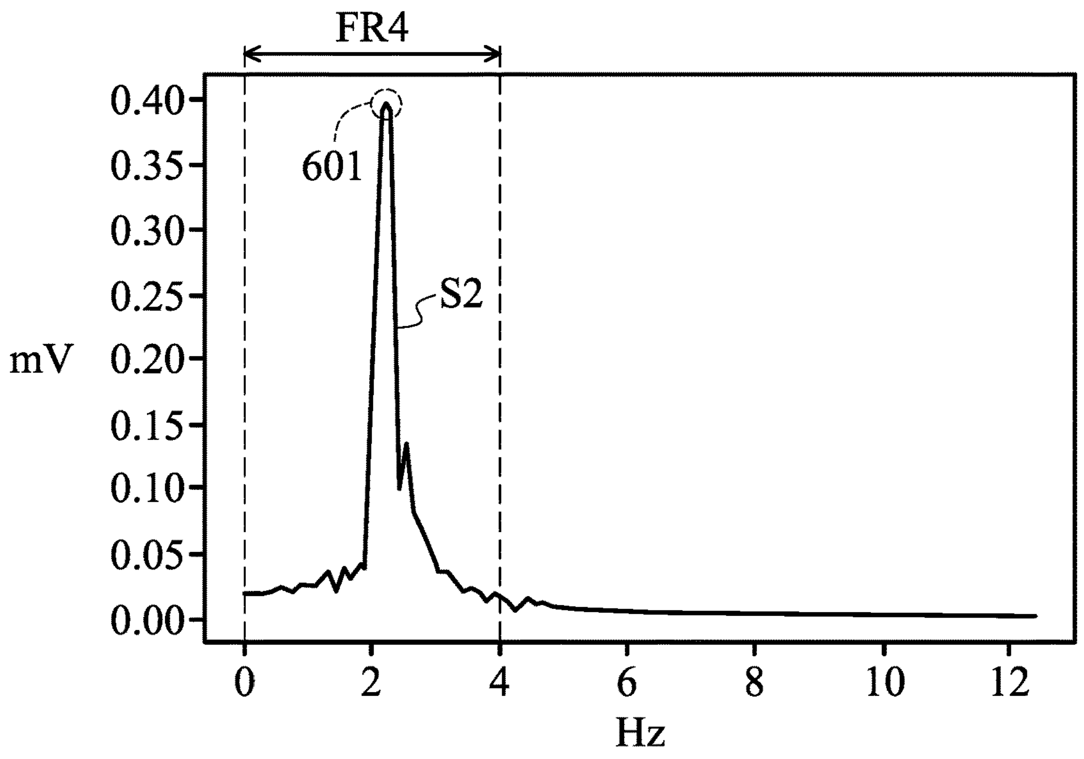
FIG. 6 is a waveform diagram of a second spectrum according an embodiment of the present invention.

As shown in FIG. 5 and FIG. 6, when determining that the frequency corresponding to the first maximum peak value (such as 501) is not the same as the frequency corresponding to the fourth maximum peak value (such as 601), the processing unit 140 may use the first maximum peak value (such as 501) as the maximum peak value corresponding to the first alternating current signal, calculate the blood oxygen value according to the first maximum peak value (such as 501) and the first direct current signal, and calculate the pulse rate according to the frequency corresponding to the first maximum peak value (such as 501).

As shown in FIG. 7 and FIG. 8 or FIG. 9 and FIG. 10, when determining that the frequency corresponding to the first maximum peak value (such as 701 or 901) is the same as the frequency corresponding to the fourth maximum peak value (such as 801 or 1001), the processing unit 140 may use a fifth frequency range (such as FR5) to search a fifth maximum peak value (such as 703 or 903) in the first spectrum, and use a sixth frequency range (such as FR6) to search a sixth maximum peak value (such as 704 or 905) in the first spectrum.

In the embodiment, the fifth frequency range (such as FR5) may partially overlap the first frequency range (such as FR1), the sixth frequency range (such as FR6) may partially overlap the first frequency range (such as FR1), and the fifth frequency range (such as FR5) may not overlap the sixth frequency range (such as FR6). For example, the fifth frequency range (such as FR5) is for example, 0.4 Hz to the frequency corresponding to the first maximum peak value (such as 701 or 901), and the sixth frequency range (such as FR6) is, for example, the frequency corresponding to the first maximum peak value (such as 701 or 901) to 4 Hz, but the embodiment of the present invention is not limited thereto.

Figure 7:
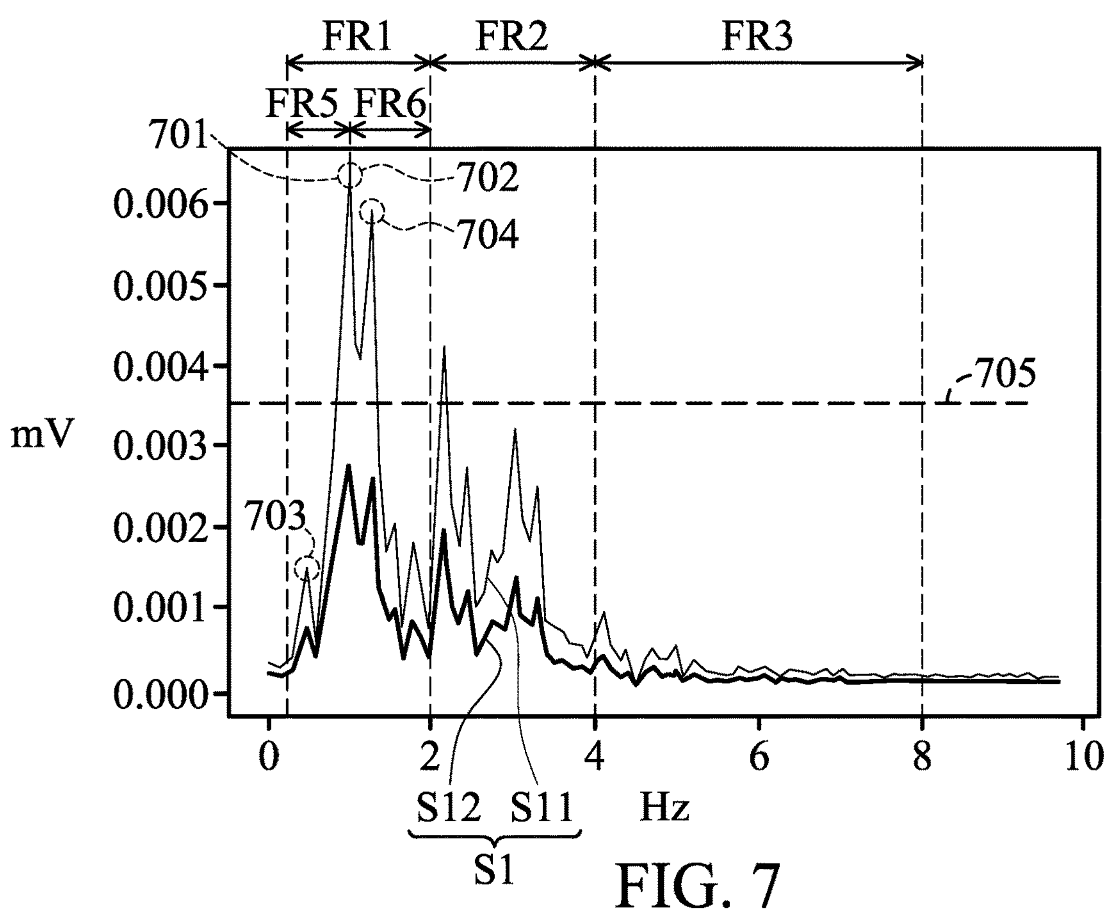
FIG. 7 is a waveform diagram of a first spectrum according an embodiment of the present invention.
Figure 8:
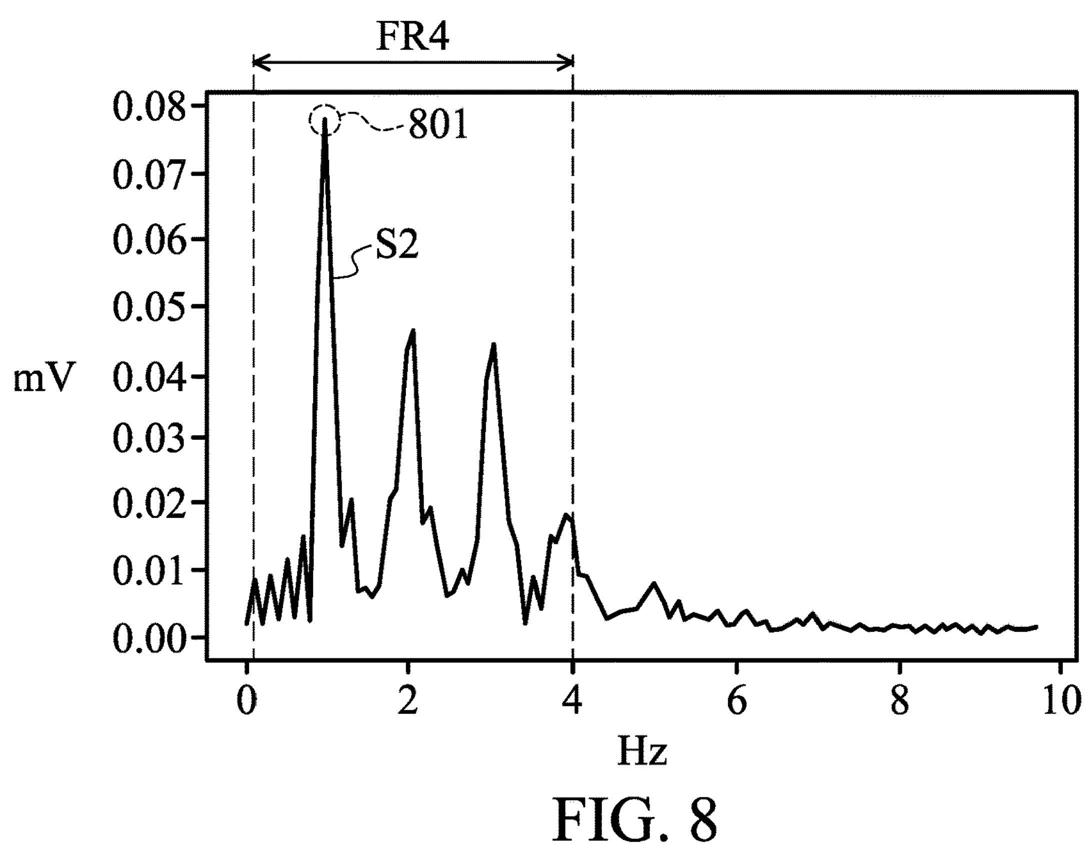
FIG. 8 is a waveform diagram of a second spectrum according an embodiment of the present invention.
Figure 9:
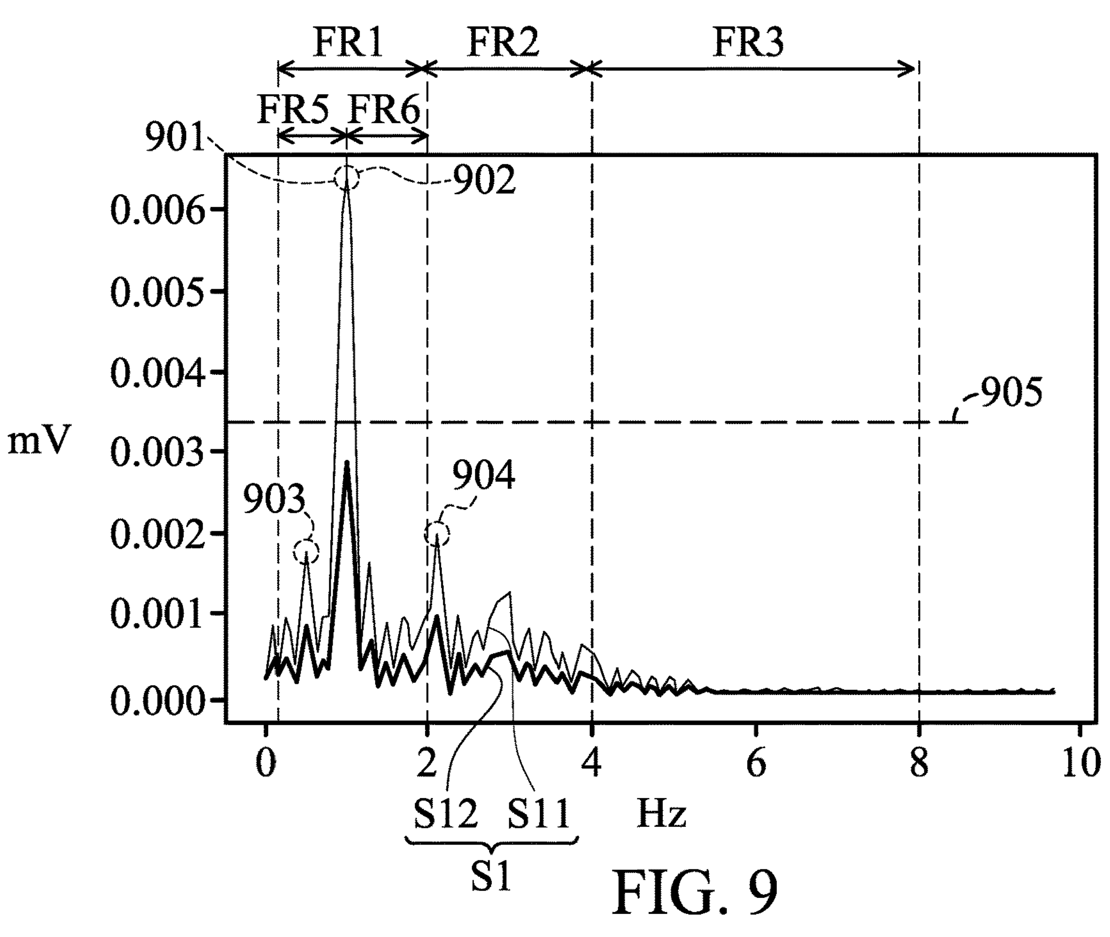
FIG. 9 is a waveform diagram of a first spectrum according an embodiment of the present invention.
Figure 10:
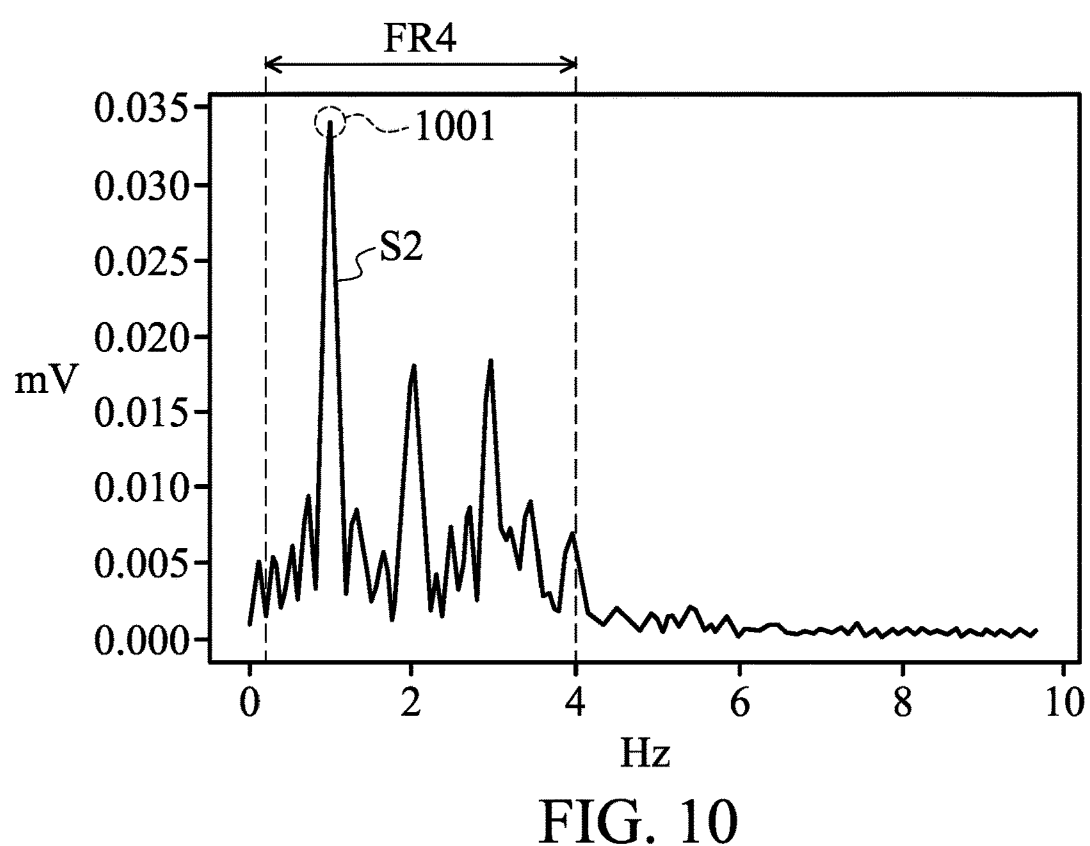
FIG. 10 is a waveform diagram of a second spectrum according an embodiment of the present invention.

As shown in FIG. 7 or FIG. 9, the processing unit 140 may determine that the fifth maximum peak value is greater than the sixth maximum peak value. When determining that the fifth maximum peak value is greater than the sixth maximum peak value, the processing unit 140 may determine whether the fifth maximum peak value is greater than a predetermined value (such as 705 or 905). In some embodiments, the above predetermined value (such as 705 or 905) may be the first maximum peak value (such as 701) multiplied by a ratio. For example, the above predetermined value (such as 705 or 905) may be the first maximum peak value (such as 701)*0.6, but the embodiment of the present application is not limited thereto.

When determining that the fifth maximum peak value is greater than the predetermined value (such as 705 or 905), the processing unit 140 may use the fifth maximum peak value as the maximum peak value corresponding to the first alternating current signal, calculate the blood oxygen value according to the fifth maximum peak value and the first direct current signal, and calculate the pulse rate according to the frequency corresponding to the fifth maximum peak value.

When determining that the fifth maximum peak value is not greater than the predetermined value (such as 705 or 905), the processing unit 140 may use the first maximum peak value (such as 701) as the maximum peak value corresponding to the first alternating current signal, calculate the blood oxygen value according to the first maximum peak value (such as 701) and the first direct current signal, and calculate the pulse rate according to the frequency corresponding to the first maximum peak value (such as 701).

Continued to the processing unit 140 determining whether the fifth maximum peak value is greater than the sixth maximum peak value, as shown in FIG. 7 or FIG. 9, when determining that the fifth maximum peak value (such as 703 or 903) is not greater than the sixth maximum peak value (such as 704 or 904), the processing unit 140 may determine whether the sixth maximum peak value (such as 704 or 904) is greater than the predetermined value (such as 705 or 905).

As show in FIG. 7, when determining that the sixth maximum peak value (such as 704) is greater than the predetermined value (such as 705), the processing unit 140 may use the fifth maximum peak value (such as 703) as the maximum peak value corresponding to the first alternating current signal, calculate the blood oxygen value according to the fifth maximum peak value (such as 703) and the first direct current signal, and calculate the pulse rate according to the frequency corresponding to the fifth maximum peak value (such as 703).

As shown in FIG. 9, when determining that the sixth maximum peak value (such as 904) is not greater than the predetermined value (such as 905), the processing unit 140 may use the first maximum peak value (such as 701) as the maximum peak value corresponding to the first alternating current signal, calculate the blood oxygen value according to the first maximum peak value (such as 701) and the first direct current signal, and calculate the pulse rate according to the frequency corresponding to the first maximum peak value (such as 701).

Figure 11:
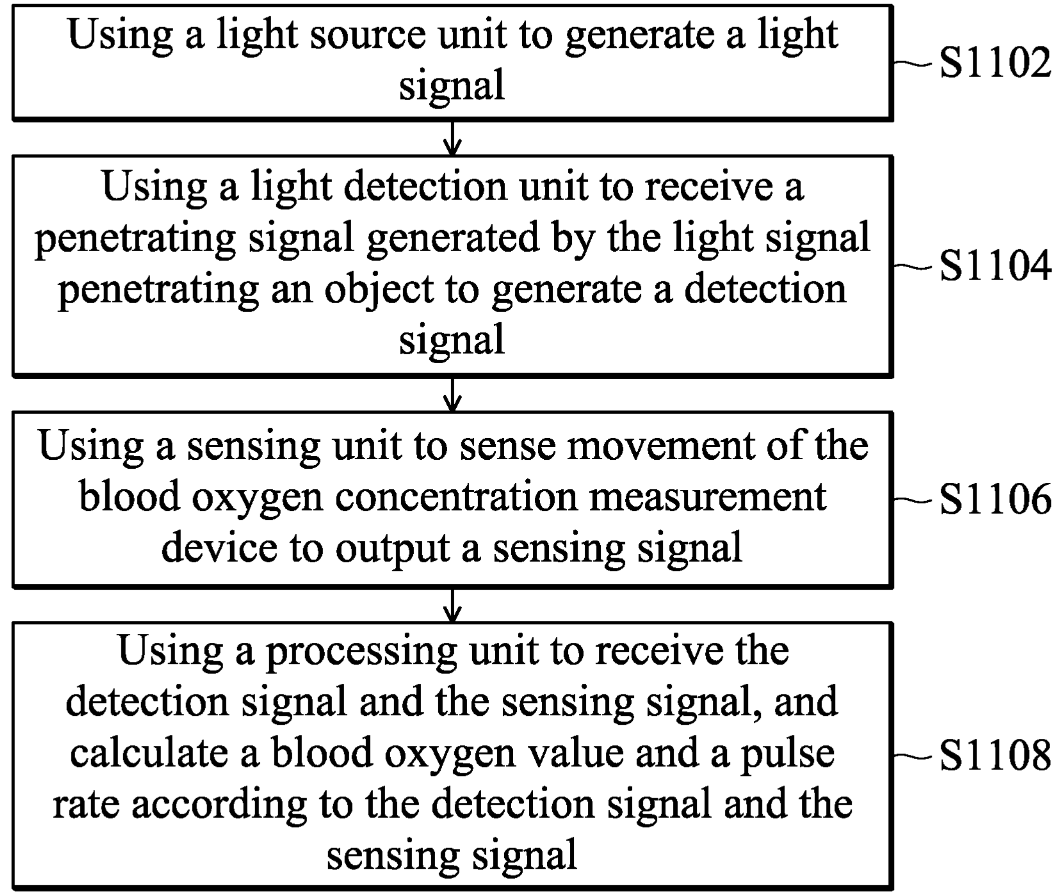
FIG. 11 is a flowchart of a blood oxygen concentration measurement method according an embodiment of the present invention.

FIG. 11 is a flowchart of a blood oxygen concentration measurement method according an embodiment of the present invention. In step S1102, the method involves using a light source unit to generate a light signal. In step S1104, the method involves using a light detection unit to receive a penetrating signal generated by the light signal penetrating an object to generate a detection signal. In step S1106, the method involves using a sensing unit to sense movement of the blood oxygen concentration measurement device to output a sensing signal. In step S1108, the method involves using a processing unit to receive the detection signal and the sensing signal, and calculate a blood oxygen value and a pulse rate according to the detection signal and the sensing signal. In the embodiment, the light signal includes, for example, a red light signal and an infrared light signal.

Figure 12:
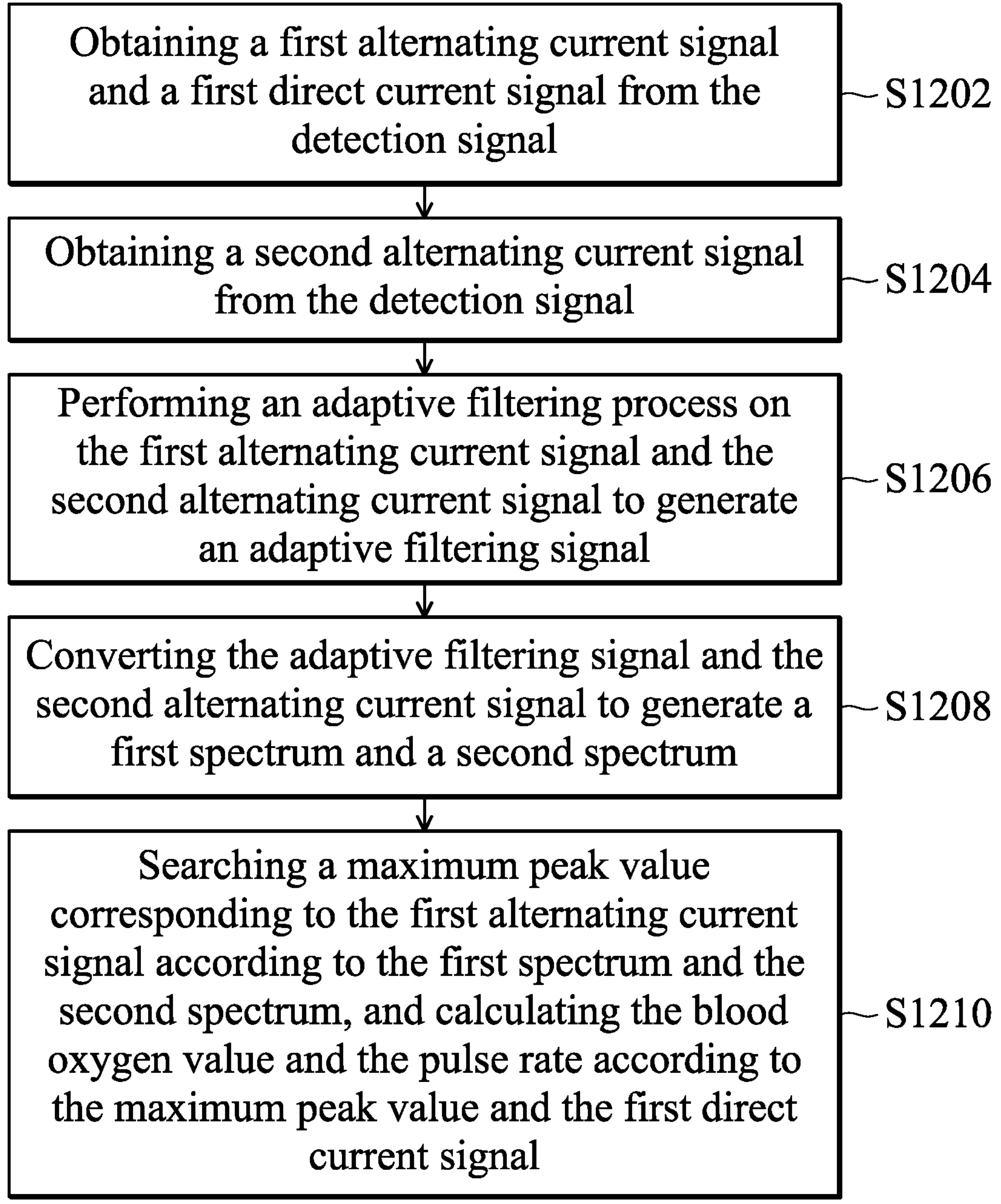
FIG. 12 is a detailed flowchart of step S1108 in FIG. 11.

FIG. 12 is a detailed flowchart of step S1108 in FIG. 11. In step S1202, the method involves obtaining a first alternating current signal and a first direct current signal from the detection signal. In step S1204, the method involves obtaining a second alternating current signal from the detection signal. In step S1206, the method involves performing an adaptive filtering process on the first alternating current signal and the second alternating current signal to generate an adaptive filtering signal. In step S1208, the method involves converting the adaptive filtering signal and the second alternating current signal to generate a first spectrum and a second spectrum. In step S1210, the method involves searching a maximum peak value corresponding to the first alternating current signal according to the first spectrum and the second spectrum, and calculating the blood oxygen value and the pulse rate according to the maximum peak value and the first direct current signal.

FIG. 13 is a detailed flowchart of step S1206 in FIG. 12. In step S1302, the method involves performing an operation on the first alternating current signal and a filtering signal to generate the adaptive filtering signal. In step S1304, the method involves performing a filtering process on the second alternating current signal and the adaptive filtering signal to generate the filtering signal.

Figure 14A:
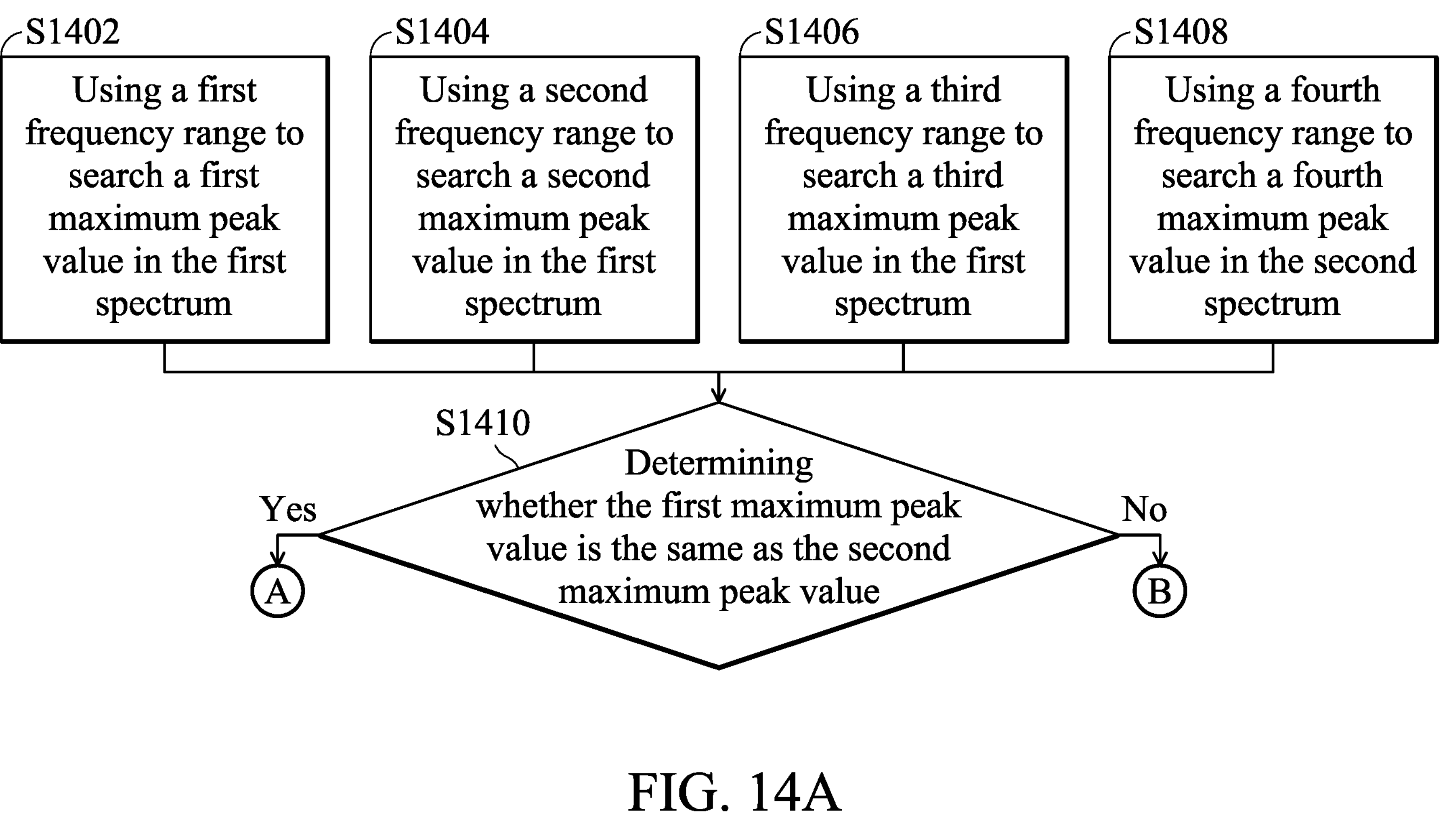
FIGS. 14A, 14B and 14C are a detailed flowchart of step S1210 in FIG. 12.
Figure 14B:
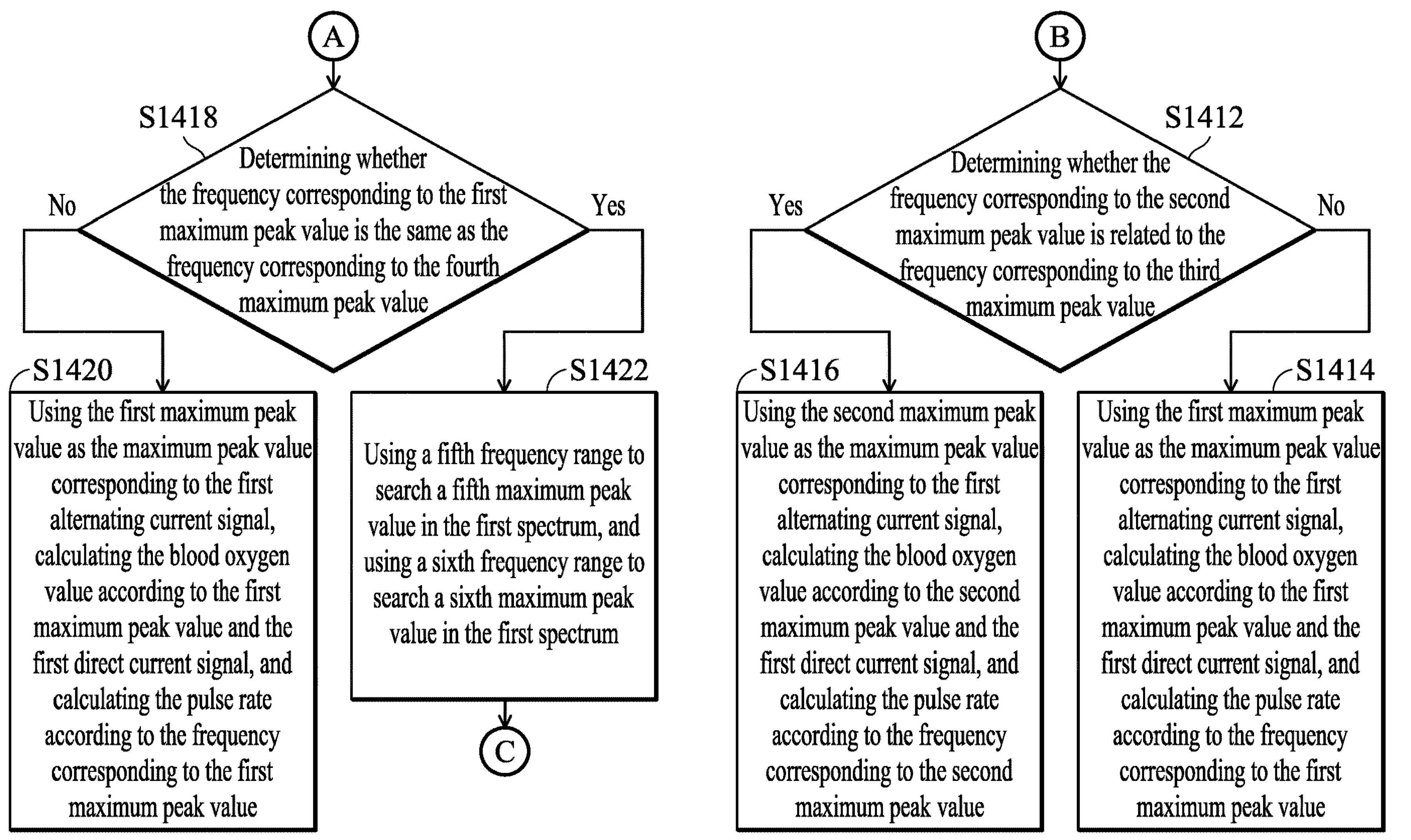
Figure 14C:
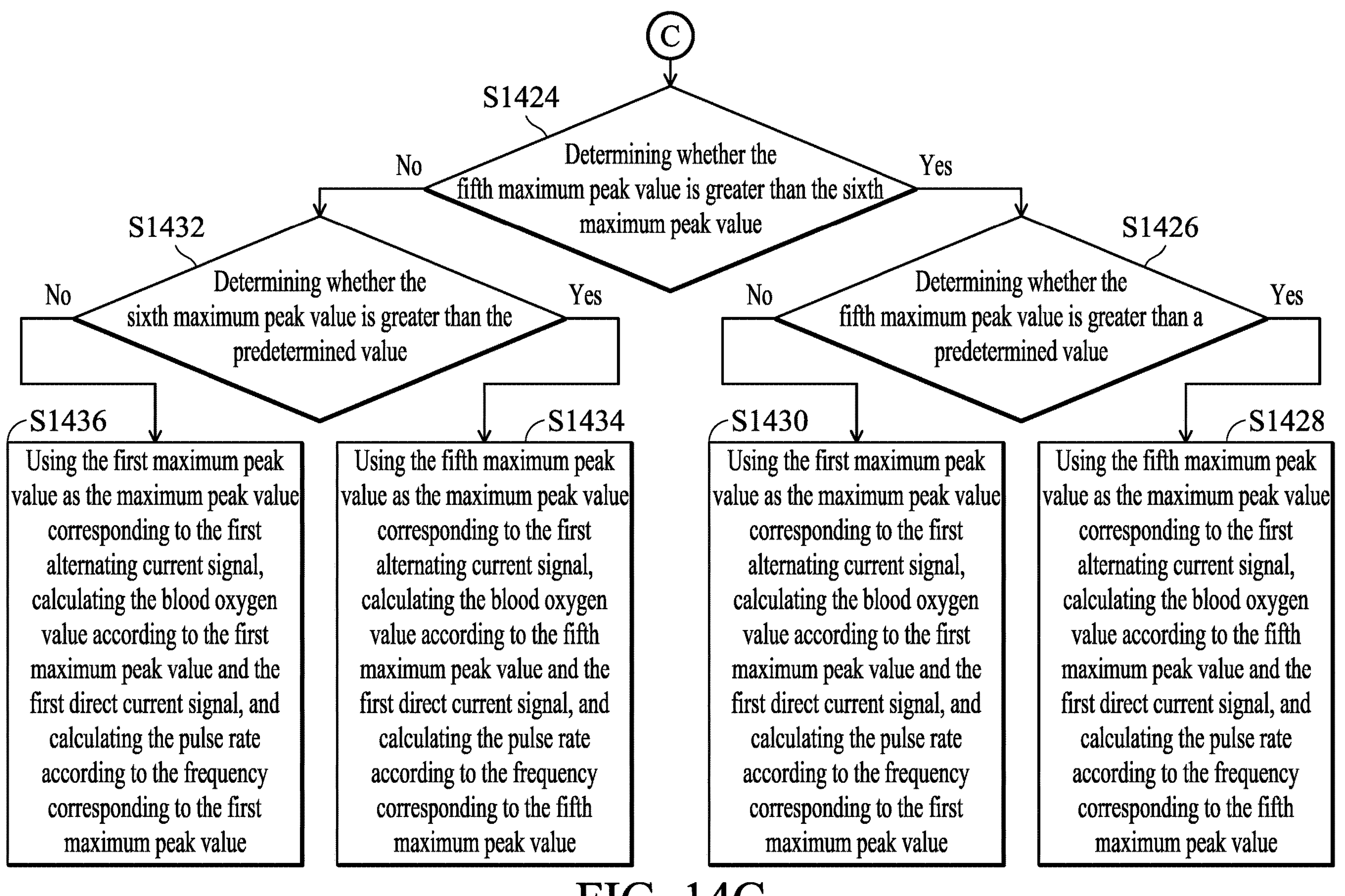

FIGS. 14A, 14B and 14C are a detailed flowchart of step S1210 in FIG. 12. In step S1402, the method involves using a first frequency range to search a first maximum peak value in the first spectrum. In step S1404, the method involves using a second frequency range to search a second maximum peak value in the first spectrum. In step S1406, the method involves using a third frequency range to search a third maximum peak value in the first spectrum. In step S1408, the method involves using a fourth frequency range to search a fourth maximum peak value in the second spectrum.

In step S1410, the method involves determining whether the first maximum peak value is the same as the second maximum peak value. When determining that the first maximum peak value is not the same as the second maximum peak value, the method performs step S1412. In step S1412, the method involves determining whether the frequency corresponding to the second maximum peak value is related to the frequency corresponding to the third maximum peak value. When the frequency corresponding to the second maximum peak value is not related to the frequency corresponding to the third maximum peak value, the method performs step S1414. In step S1414, the method involves using the first maximum peak value as the maximum peak value corresponding to the first alternating current signal, calculating the blood oxygen value according to the first maximum peak value and the first direct current signal, and calculating the pulse rate according to the frequency corresponding to the first maximum peak value.

When the frequency corresponding to the second maximum peak value is related to the frequency corresponding to the third maximum peak value, the method performs step S1416. In step S1416, the method involves using the second maximum peak value as the maximum peak value corresponding to the first alternating current signal, calculating the blood oxygen value according to the second maximum peak value and the first direct current signal, and calculating the pulse rate according to the frequency corresponding to the second maximum peak value.

Continued to step S1410, when determining that the first maximum peak value is the same as the second maximum peak value, the method performs step S1418. In step S1418, the method involves determining whether the frequency corresponding to the first maximum peak value is the same as the frequency corresponding to the fourth maximum peak value. When determining that the frequency corresponding to the first maximum peak value is not the same as the frequency corresponding to the fourth maximum peak value, the method performs step S1420. In step S1420, the method involves using the first maximum peak value as the maximum peak value corresponding to the first alternating current signal, calculating the blood oxygen value according to the first maximum peak value and the first direct current signal, and calculating the pulse rate according to the frequency corresponding to the first maximum peak value.

When determining that the frequency corresponding to the first maximum peak value is the same as the frequency corresponding to the fourth maximum peak value, the method performs step S1422. In step S1422, the method involves using a fifth frequency range to search a fifth maximum peak value in the first spectrum, and using a sixth frequency range to search a sixth maximum peak value in the first spectrum.

In step S1424, the method involves determining whether the fifth maximum peak value is greater than the sixth maximum peak value. When determining that the fifth maximum peak value is greater than the sixth maximum peak value, the method performs step S1426. In step S1426, the method involves determining whether the fifth maximum peak value is greater than a predetermined value. When determining that the fifth maximum peak value is greater than the predetermined value, the method performs step S1428. In step S1428, the method involves using the fifth maximum peak value as the maximum peak value corresponding to the first alternating current signal, calculating the blood oxygen value according to the fifth maximum peak value and the first direct current signal, and calculating the pulse rate according to the frequency corresponding to the fifth maximum peak value.

When determining that the fifth maximum peak value is not greater than the predetermined value, the method performs step S1430. In step S1430, the method involves using the first maximum peak value as the maximum peak value corresponding to the first alternating current signal, calculating the blood oxygen value according to the first maximum peak value and the first direct current signal, and calculating the pulse rate according to the frequency corresponding to the first maximum peak value.

Continued to S1424, when determining that the fifth maximum peak value is not greater than the sixth maximum peak value, the method performs step S1432. In step S1432, the method involves determining whether the sixth maximum peak value is greater than the predetermined value.

When determining that the sixth maximum peak value is greater than the predetermined value, the method performs step S1434. In step S1434, the method involves using the fifth maximum peak value as the maximum peak value corresponding to the first alternating current signal, calculating the blood oxygen value according to the fifth maximum peak value and the first direct current signal, and calculating the pulse rate according to the frequency corresponding to the fifth maximum peak value.

When determining that the sixth maximum peak value is not greater than the predetermined value, the method performs step S1436. In step S1436, the method involves using the first maximum peak value as the maximum peak value corresponding to the first alternating current signal, calculating the blood oxygen value according to the first maximum peak value and the first direct current signal, and calculating the pulse rate according to the frequency corresponding to the first maximum peak value. In the embodiment, the first frequency range partially overlaps the second frequency range, the second frequency range does not overlap the third frequency range, the second frequency range overlaps the fourth frequency range, the fifth frequency range partially overlaps the first frequency range, the sixth frequency range partially overlaps the first frequency range, and the fifth frequency range does not overlap the sixth frequency range.

In summary, according to the blood oxygen concentration measurement device and method disclosed by the embodiment of the present invention, the light detection unit receives the penetrating signal generated by the light signal penetrating the object to generate the detection signal, the sensing unit senses the movement of the blood oxygen concentration measurement device to output the sensing signal, and the processing unit calculates the blood oxygen value and the pulse rate according to the detection signal and the sensing signal. Therefore, the accuracy of the blood oxygen concentration measurement may be effectively increased under the object actives, and the convenience of use is increased.

While the present invention has been described by way of example and in terms of the preferred embodiments, it should be understood that the present invention is not limited to the disclosed embodiments. On the contrary, it is intended to cover various modifications and similar arrangements (as would be apparent to those skilled in the art). Therefore, the scope of the appended claims should be accorded the broadest interpretation to encompass all such modifications and similar arrangements.

What is claimed is:

1. A blood oxygen concentration measurement device, comprising:

a light source unit, configured to generate a light signal;

a light detection unit, configured to receive a penetrating signal generated by the light signal penetrating an object to generate a detection signal;

a sensing unit, configured to sense movement of the blood oxygen concentration measurement device to output a sensing signal; and a processing unit, configured to receive the detection signal and the sensing signal, and calculate a blood oxygen value and a pulse rate according to the detection signal and the sensing signal;

wherein the processing unit obtains a first alternating current signal and a first direct current signal from the detection signal, obtains a second alternating current signal from the detection signal, performs an adaptive filtering process on the first alternating current signal and the second alternating current signal to generate an adaptive filtering signal, converts the adaptive filtering signal and the second alternating current signal to generate a first spectrum and a second spectrum, searches a maximum peak value corresponding to the first alternating current signal according to the first spectrum and the second spectrum, and calculates the blood oxygen value and the pulse rate according to the maximum peak value and the first direct current signal.

2. The blood oxygen concentration measurement device as claimed in claim 1, wherein the light signal comprises a red light signal and an infrared light signal.

3. The blood oxygen concentration measurement device as claimed in claim 1, wherein the processing unit performs an operation on the first alternating current signal and a filtering signal to generate the adaptive filtering signal, and performs a filtering process on the second alternating current signal and the adaptive filtering signal to generate the filtering signal.

4. The blood oxygen concentration measurement device as claimed in claim 1, wherein the processing unit uses a first frequency range to search a first maximum peak value in the first spectrum, the processing unit uses a second frequency range to search a second maximum peak value in the first spectrum, and the processing unit uses a third frequency range to search a third maximum peak value in the first spectrum;

the processing unit determines whether the first maximum peak value is the same as the second maximum peak value;

when determining that the first maximum peak value is not the same as the second maximum peak value, the processing unit determines whether a frequency corresponding to the second maximum peak value is related to a frequency corresponding to the third maximum peak value;

when the frequency corresponding to the second maximum peak value is not related to the frequency corresponding to the third maximum peak value, the processing unit uses the first maximum peak value as the maximum peak value corresponding to the first alternating current signal, calculates the blood oxygen value according to the first maximum peak value and the first direct current signal, and calculates the pulse rate according to a frequency corresponding to the first maximum peak value.

5. The blood oxygen concentration measurement device as claimed in claim 4, wherein when the frequency corresponding to the second maximum peak value is related to the frequency corresponding to the third maximum peak value, the processing unit uses the second maximum peak value as the maximum peak value corresponding to the first alternating current signal, calculates the blood oxygen value according to the second maximum peak value and the first direct current signal, and calculates the pulse rate according to the frequency corresponding to the second maximum peak value.

6. The blood oxygen concentration measurement device as claimed in claim 4, wherein when the first maximum peak value is the same as the second maximum peak value, the processing unit uses a fourth frequency range to search a fourth maximum peak value in the second spectrum, and the processing unit determines whether the frequency corresponding to the first maximum peak value is the same as a frequency corresponding to the fourth maximum peak value;

when determining that the frequency corresponding to the first maximum peak value is not the same as the frequency corresponding to the fourth maximum peak value, the processing unit uses the first maximum peak value as the maximum peak value corresponding to the first alternating current signal, calculates the blood oxygen value according to the first maximum peak value and the first direct current signal, and calculates the pulse rate according to the frequency corresponding to the first maximum peak value.

7. The blood oxygen concentration measurement device as claimed in claim 6, wherein when determining that the frequency corresponding to the first maximum peak value is the same as the frequency corresponding to the fourth maximum peak value, the processing unit uses a fifth frequency range to search a fifth maximum peak value in the first spectrum, and uses a sixth frequency range to search a sixth maximum peak value in the first spectrum;

the processing unit determines whether the fifth maximum peak value is greater than the sixth maximum peak value;

when determining that the fifth maximum peak value is greater than the sixth maximum peak value, the processing unit determines whether the fifth maximum peak value is greater than a predetermined value;

when determining that the fifth maximum peak value is greater than the predetermined value, the processing unit uses the fifth maximum peak value as the maximum peak value corresponding to the first alternating current signal, calculates the blood oxygen value according to the fifth maximum peak value and the first direct current signal, and calculates the pulse rate according to a frequency corresponding to the fifth maximum peak value.

8. The blood oxygen concentration measurement device as claimed in claim 7, wherein when determining that the fifth maximum peak value is not greater than the predetermined value, the processing unit uses the first maximum peak value as the maximum peak value corresponding to the first alternating current signal, calculates the blood oxygen value according to the first maximum peak value and the first direct current signal, and calculates the pulse rate according to the frequency corresponding to the first maximum peak value.

9. The blood oxygen concentration measurement device as claimed in claim 7, wherein when determining that the fifth maximum peak value is not greater than the sixth maximum peak value, the processing unit determines whether the sixth maximum peak value is greater than the predetermined value;

when determining that the sixth maximum peak value is greater than the predetermined value, the processing unit uses the fifth maximum peak value as the maximum peak value corresponding to the first alternating current signal, calculates the blood oxygen value according to the fifth maximum peak value and the first direct current signal, and calculates the pulse rate according to the frequency corresponding to the fifth maximum peak value.

10. The blood oxygen concentration measurement device as claimed in claim 9, wherein when determining that the sixth maximum peak value is not greater than the predetermined value, the processing unit uses the first maximum peak value as the maximum peak value corresponding to the first alternating current signal, calculates the blood oxygen value according to the first maximum peak value and the first direct current signal, and calculates the pulse rate according to the frequency corresponding to the first maximum peak value.

11. A blood oxygen concentration measurement method, comprising:

using a light source unit to generate a light signal;

using a light detection unit to receive a penetrating signal generated by the light signal penetrating an object to generate a detection signal;

using a sensing unit to sense movement of a blood oxygen concentration measurement device to output a sensing signal; and using a processing unit to receive the detection signal and the sensing signal, and to calculate a blood oxygen value and a pulse rate according to the detection signal and the sensing signal;

wherein the processing unit obtains a first alternating current signal and a first direct current signal from the detection signal, obtains a second alternating current signal from the detection signal, performs an adaptive filtering process on the first alternating current signal and the second alternating current signal to generate an adaptive filtering signal, converts the adaptive filtering signal and the second alternating current signal to generate a first spectrum and a second spectrum, searches a maximum peak value corresponding to the first alternating current signal according to the first spectrum and the second spectrum, and calculates the blood oxygen value and the pulse rate according to the maximum peak value and the first direct current signal.

* * * * *